United States Patent [19]

Kert et al.

[11] Patent Number: 5,252,828
[45] Date of Patent: Oct. 12, 1993

[54] MOBILE EXHAUST TRACKING SYSTEM

[75] Inventors: John Kert, Hermosa Beach; Nelson W. Sorbo, Canoga Park, both of Calif.

[73] Assignee: Hughes Aircraft Company, Los Angeles, Calif.

[21] Appl. No.: 864,832

[22] Filed: Apr. 7, 1992

[51] Int. Cl.⁵ .......................... G01N 21/01; G01J 3/00
[52] U.S. Cl. ................... 250/339; 250/338.5; 356/438
[58] Field of Search ............ 250/253, 255, 339, 338.5, 250/343, 340; 356/438, 439

[56] References Cited

U.S. PATENT DOCUMENTS

| | | | |
|---|---|---|---|
| 2,879,663 | 3/1959 | Thomas | 250/343 X |
| 3,023,310 | 2/1962 | Maxwell | 250/255 |
| 3,640,624 | 2/1972 | Anderson et al. | 356/439 X |
| 3,696,247 | 10/1972 | McIntosh et al. | 250/343 X |
| 4,323,777 | 4/1982 | Baskins et al. | 250/339 |
| 4,748,336 | 5/1988 | Fujie et al. | |
| 4,801,805 | 1/1989 | Butler et al. | 250/343 |
| 4,818,705 | 4/1989 | Schneider et al. | 250/343 X |
| 5,138,163 | 8/1992 | Butler et al. | 250/343 X |

FOREIGN PATENT DOCUMENTS 62-52439  3/1987  Japan .................. 356/439

*Primary Examiner*—Constantine Hannaher
*Assistant Examiner*—Edward J. Glick
*Attorney, Agent, or Firm*—Terje Gudmestad; Michael W. Sales; Wanda K. Denson-Low

[57] ABSTRACT

This invention relates to an apparatus (10) for, and a method of, collecting and analyzing a sample of exhaust gases (16) from a mobile exhaust source. A funneling member (18) is attached to a vehicle (12) for concentrating exhaust gases (16) discharged by a moving exhaust source. The vehicle (12) is positioned behind the mobile exhaust source such that the funneling member (18) is within a stream of exhaust gases (30) being discharged by the mobile exhaust source. As the exhaust gases (16) pass through the funneling member (18), a sampling tube (22) extracts a sample of the concentrated exhaust gases (16) and routes them to an analyzing means (26) for analysis of the sample.

7 Claims, 3 Drawing Sheets

MOBILE EXHAUST TRACKING SYSTEM

BACKGROUND OF THE INVENTION

TECHNICAL FIELD

This invention relates generally to exhaust analyzing systems and, more particularly to a mobile, exhaust analyzing system capable of collecting and analyzing exhaust gases from a moving source vehicle by following it.

DISCUSSION

Exhaust analyzing systems are utilized for measuring and analyzing exhaust gases discharged by motor vehicles. Existing technology is generally limited to crossroad, single lane measurement systems. These systems utilize stationary measuring devices to measure and analyze exhaust gases from motor vehicles as the motor vehicles pass by. These types of stationary systems do not provide practical means to police high polluting vehicles on public roadways. First of all, the vehicle must pass by the testing system, and second, a concentrated sample of the exhaust gases cannot be easily collected. Therefore, it is desirable to use a mobile test system that can collect exhaust gas samples on multilane freeways, highways and streets. It is also desirable to have a system that samples exhaust gases continuously, thereby eliminating inconsistencies and allowing for the of exhaust gases, a dispersive spectrometer such as a Fourier transfer infrared spectrophotometer may be used rather than a low spectral resolution non-dispersive filter spectrometer.

SUMMARY OF THE INVENTION

The present invention relates to a mobile, exhaust analyzing apparatus having a carrying means, a collecting means and an analyzing means. The collecting means is utilized for collecting exhaust gas samples and is attached to the carrying means such that the collecting means can be transported to a location for taking samples, and such that the collecting means can take samples while being moved by the carrying means. The analyzing means is utilized for analyzing the samples collected.

DETAILED DESCRIPTION OF THE PREFERRED EMBODIMENT

Figure 1:
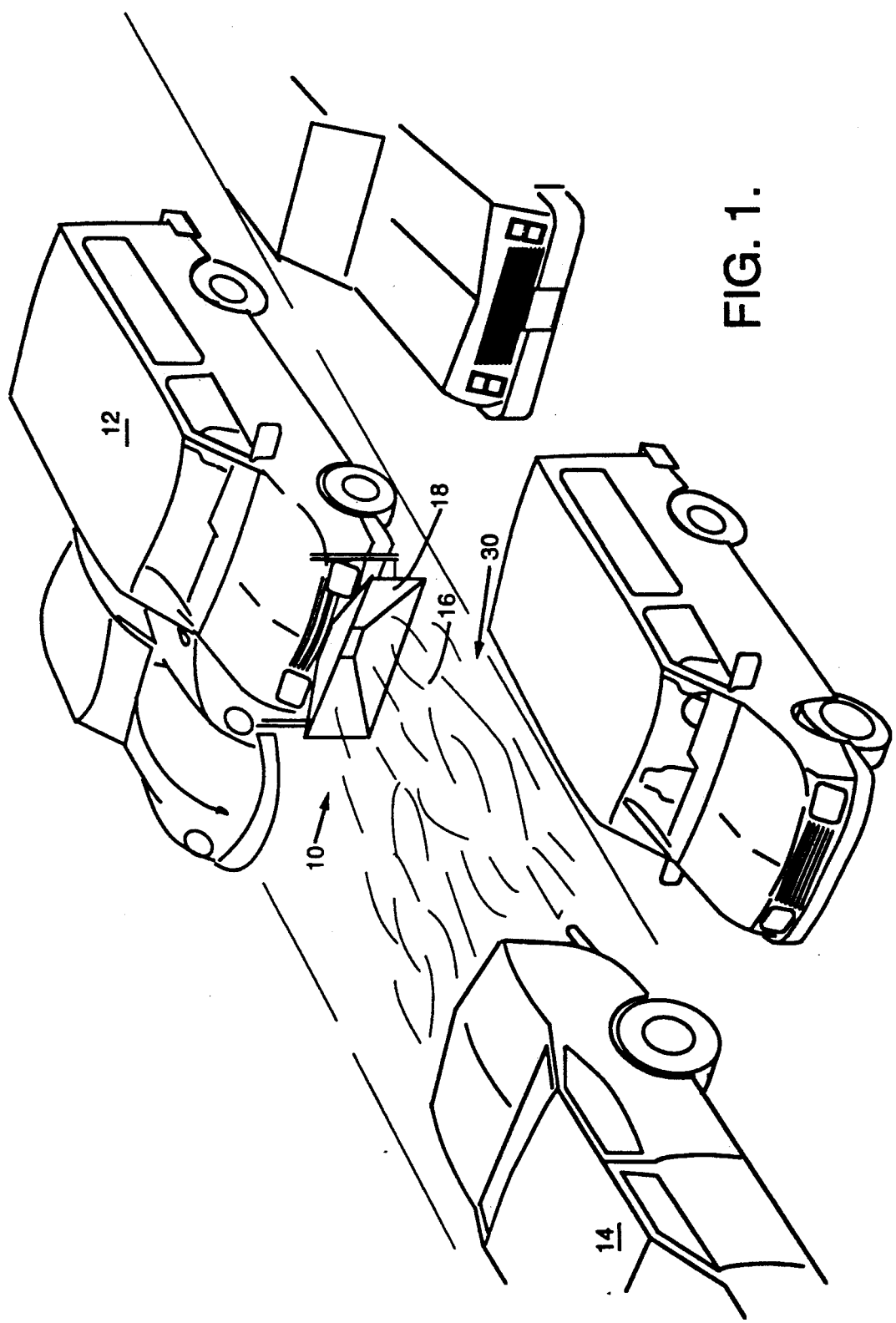
FIG. 1 is a perspective illustration of a funneling device mounted to the front of a vehicle, showing the vehicle positioned such that the funneling device is within the stream of exhaust gases being discharged from the car directly in front of it.
Figure 2:
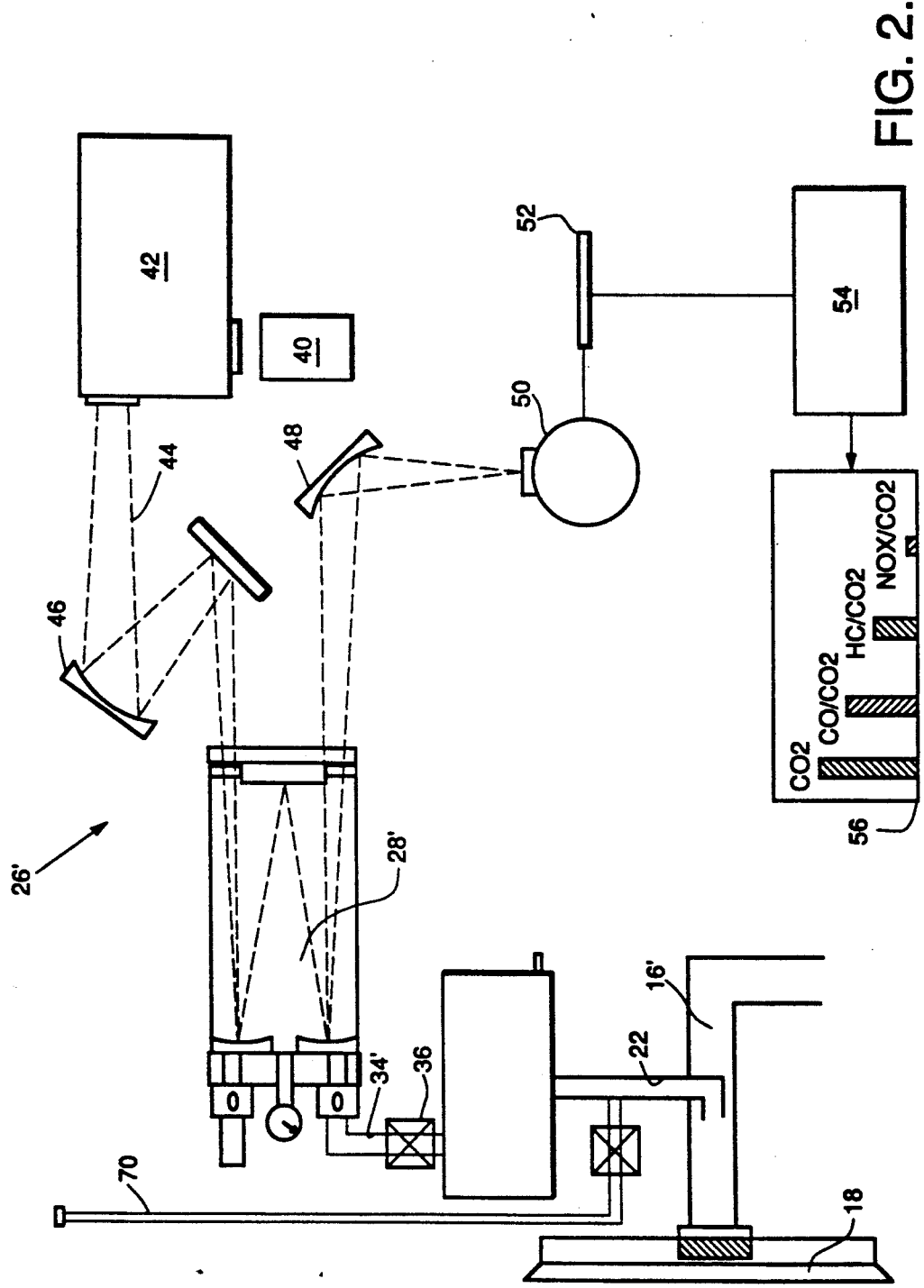
FIG. 2 is a diagrammatic view of a mobile, exhaust analyzing apparatus in accordance with the principles of the present invention illustrating an exhaust gas sampling apparatus coupled to a dispersive spectrophotometer which analyzes the exhaust gas, and a computer that processes information from the spectrophotometer.

Referring now to the drawings, and more particularly to FIG. a mobile, exhaust analyzing apparatus 10 is shown. The embodiment depicted in FIG. 1 illustrates a test vehicle 12 following an exhaust source vehicle 14 in an attempt to collect a sample of exhaust gases 16 from the source vehicle 14. The test vehicle 12 utilizes a funneling member 18 to concentrate exhaust gases 16 discharged by the source vehicle 14. As best shown in FIG. 2, once the exhaust gases 16 are concentrated by the funneling member 18, the gases 16 pass through a filter 20 and into a sampling tube 22. The gases then pass through a condenser 24 and into an exhaust analyzer 26 where the composition of the gas 16 is determined.

By collecting and analyzing exhaust gases 16 with an on-board system, larger and more consistent samples 28 are able to be obtained. While traditional exhaust analyzing systems are only capable of taking samples as vehicles pass close by, this on-board system is easily maneuvered into, and kept within, a stream of exhaust gases being discharged by a moving vehicle. This is accomplished by simply positioning the test vehicle 12 such that the funneling member 18 is within the source vehicle's exhaust plume 30. Depending on conditions such as weather, traffic, road curvature, etc., a typical exhaust plume 30 will extend from the source vehicle 14 as far back as 100 to 150 feet. Thus, so long as the funneling member 18 is kept within the exhaust plume 30, a continuous stream of exhaust gases 16 passes through the funneling member 18 and is available for sampling.

The embodiment depicted in FIG. 2 illustrates that as the exhaust gases 16 pass through the funneling member 18, they are concentrated and passed through the filter 20 which removes undesirable road particulates from the exhaust stream. After the exhaust gases 16 are filtered, the gases pass through duct work that extends rearward from the funneling member 18 toward the rear of the test vehicle 12. As shown in FIG. 2, sampling tube 22 is positioned within a duct 32 to extract a sample 28 of the exhaust gases 16 as the gases 16 pass through the duct work. In this embodiment, the sampling tube 22 is placed in the middle of the duct 32 to avoid any boundary layer effects the gases 16 encounter as they stream past the edges of the duct work. Once the exhaust gases 16 enter the sampling tube 22, they pass through it and into a condenser 24 where any water within the sample 28 is removed. After the water is removed from the sample 28, the sample 28 is permitted to pass through a transport tube 34 to the analyzing apparatus 26 where analysis on the sample 28 is performed. Note that this transport tube 34 utilizes a valve 36 to either permit or prevent the sample 28 from entering the analyzing apparatus 26.

The analyzing apparatus 26 shown in FIG. 2 is a conventional Fourier transform infrared spectrophotometer. More particularly, an infrared source 40 generates infrared radiation which passes through a Fourier transform infrared device (FTIR) 42. This FTIR 42 modulates, splits and projects the radiation 44 to a series of reflecting devices 46 before this radiation 44 enters the white cell 38. The embodiment depicted in FIG. 2 utilizes two reflecting devices 46 between the FTIR 42 and the white cell 38, however, one of ordinary skill in the art would certainly recognize that a variety of configurations using any number of reflecting devices 46 could be utilized to redirect the radiation. The white cell 38 shown in FIG. 2 is a conventional white cell that holds the sample 28 while interferograms are taken.

Modulated radiation 44 passes through the sample 28 within the white cell 38 and eventually exits the white cell 38. It then strikes a focusing reflective device 48 before entering a conventional detector 50. The detector 50 produces an analog signal containing information that indicates what components are present. This analog signal is fed through a conventional analog-to-digital interface 52 and into a computer 54. The computer 54 uses conventional software packages to analyze the information and generate various types of data 56 such as ratios of various compounds to carbon dioxide and the like.

Figure 3:
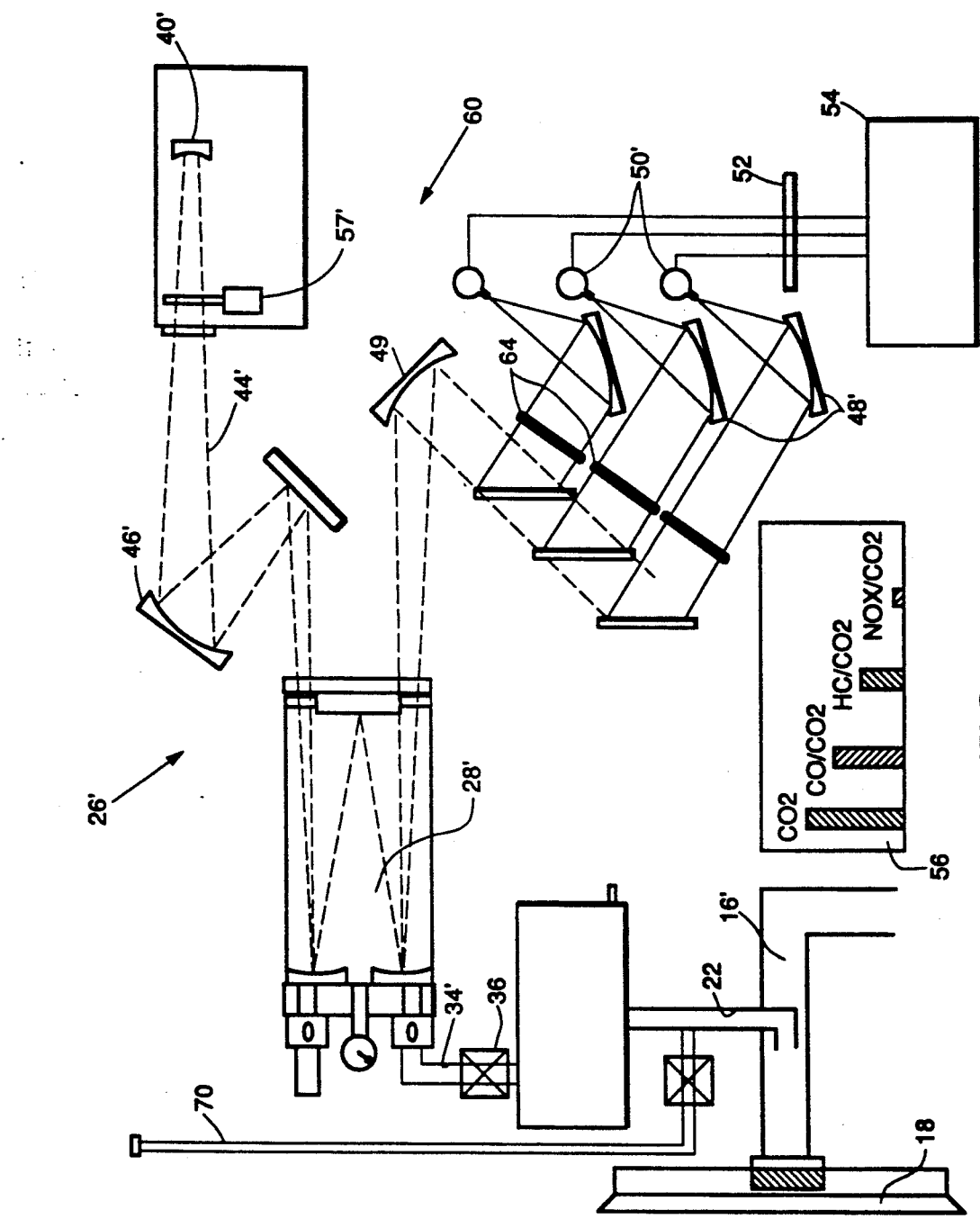
FIG. 3 is a diagrammatic view of a mobile, exhaust analyzing apparatus in accordance with the principles of an alternative embodiment of the present invention illustrating an exhaust gas sampling apparatus coupled to a non-dispersive spectrometer which analyzes the exhaust gas, and a computer that processes information from the spectrometer.

As shown in FIG. 3, a filter spectrometer 60 can instead be utilized as an analyzing apparatus 26'. The filter spectrometer 60, unlike the spectrophotometer discussed above, is a non-dispersive device. When this type of filter spectrometer 60 is utilized, gases 16' pass from the condenser 24' through the transport tube 34' and into a white cell 38, as shown in FIG. 3. Infrared radiation 44' is then directed into the white cell 38 by reflective devices 46'. Note that this radiation 44' is generated by a conventional infrared radiation generator 40' and passes through a conventional chopper 57 prior to entering the white cell 38.

Once the sample 28' is in the white cell 38, measurements can be taken by an optical filter arrangement 55. This optical filter arrangement 55 receives radiation 44' from the white cell 38 via a reflective device 49. The radiation 44' reflects off the reflective device 48' and into a series of conventional beam splitters 62. The beam splitters 62 redirect the radiation through conventional filters 64 that filter out undesirable bands of radiation. The filtered radiation then strikes a series of focusing reflective devices 48' before passing into detectors 50', through an analog-to-digital interface 52 and into a computer 54 for analysis. Computer analysis produces data 56' such as ratios, of carbon monoxide to carbon dioxide, hydrocarbons to carbon dioxide and the like.

In one application, the exhaust analyzing apparatus 10 can be utilized for policing polluting vehicles and enforcing environmental regulation standards. Accordingly, a test vehicle 12 would patrol streets, freeways and highways taking instantaneous measurements from any number of source vehicles 14. If a vehicle is found to be exceeding the environmental regulation standards, the vehicle owner can be notified of the problem, or alternatively pulled over for a more accurate measurement. As best shown in FIG. 2, this more accurate measurement can be taken by inserting an external probe unit 70 directly into the tailpipe of the source vehicle 14. Exhaust gases 16 taken directly from the tailpipe of the source vehicle 14 pass from the external probe 70 and into the condenser 24 for removal of any water. The exhaust gas sample 28 is then routed to the analyzing apparatus 26 via a transport tube 34 that utilizes a valve 36 to permit or prevent the sample 28 from entering the analyzing apparatus 26. The sample 28 is then analyzed in the same manner set forth above. Since this method samples exhaust gases 16 directly from the source vehicle's exhaust system, a more accurate reading can be obtained and an official determination of whether or not the source vehicle 14 is emitting pollutants in excess of environmental regulation standards can be made.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

We claim:

1. A mobile, exhaust analyzing apparatus comprising:
   (a) a first vehicle;
   (b) a funneling member attached to said first vehicle for concentrating exhaust gases discharged by a moving, second vehicle, said funneling member concentrating said exhaust gases as said gases pass through said funneling member;
   (c) sampling means, connected to the funneling member, for extracting a sample of said exhaust gases; and
   (d) a specrophotometer for analyzing said sample of said exhaust gases to determine whether the exhaust from the second vehicle exceeds environmental regulation standards.

2. The exhaust analyzing apparatus of claim 1 wherein said spectrophotometer is disposed within said first vehicle.

3. The exhaust analyzing apparatus of claim 1 wherein said sampling means further comprises an external probe unit that extracts an exhaust gas sample directly from said second vehicle when said second vehicle is stationary.

4. The exhaust analyzing apparatus of claim 1 wherein said sampling means includes a condenser for removing water from said sample.

5. A method for collecting and analyzing a sample of exhaust gases from an exhaust stream created by a moving automotive vehicle, said method comprising the steps of:
   (a) securing collecting means to a first automotive vehicle;
   (b) positioning said first vehicle such that said collecting means is within a stream of exhaust gases being discharged from a moving, second automotive vehicle;
   (c) collecting a sample of said exhaust gases from said stream of exhaust gases; and
   (d) analyzing said sample to determine whether the composition of the exhaust being discharged by said second vehicle exceeds environmental regulation standards.

6. The method of claim 5 wherein said step of securing the collecting means to a first vehicle involves mounting a funneling member to the front of said vehicle.

7. The method of claim 5 wherein said step of collecting a sample of said exhaust gases further comprises the step of passing said sample through a condenser thereby removing water from said sample.

* * * * *